United States Patent [19]

Wong et al.

[11] Patent Number: 5,198,229
[45] Date of Patent: Mar. 30, 1993

[54] SELF-RETAINING GASTROINTESTINAL DELIVERY DEVICE

[75] Inventors: Patrick S. L. Wong, Palo Alto; Felix Theeuwes, Los Altos; Steven D. Larsen, Dublin, all of Calif.

[73] Assignee: ALZA Corporation, Palo Alto, Calif.

[21] Appl. No.: 710,607

[22] Filed: Jun. 5, 1991

[51] Int. Cl.[5] .............................................. A61K 9/24
[52] U.S. Cl. .................................... 424/473; 424/422; 424/438; 424/451
[58] Field of Search ................ 424/473, 438, 451, 422

[56] References Cited

U.S. PATENT DOCUMENTS

| | | | |
|---|---|---|---|
| 3,786,813 | 1/1974 | Michaels | 128/260 |
| 3,788,322 | 1/1974 | Michaels | 128/260 |
| 3,797,492 | 3/1974 | Place | 128/260 |
| 3,845,770 | 11/1974 | Theeuwes et al. | 128/260 |
| 3,865,108 | 2/1975 | Hartop | 128/260 |
| 3,901,232 | 8/1975 | Michaels et al. | 128/260 |
| 3,916,899 | 11/1975 | Theeuwes et al. | 128/260 |
| 3,976,764 | 8/1976 | Watanabe | 424/451 |
| 3,995,631 | 12/1976 | Higuchi et al. | 128/260 |
| 4,002,173 | 1/1977 | Manning et al. | 128/296 |
| 4,034,756 | 7/1977 | Higuchi et al. | 128/260 |
| 4,063,064 | 12/1977 | Saunders et al. | 219/121 L |
| 4,088,864 | 5/1978 | Theeuwes et al. | 219/121 LM |
| 4,111,202 | 9/1978 | Theeuwes | 128/260 |
| 4,200,098 | 4/1980 | Ayer et al. | 128/260 |
| 4,207,890 | 6/1980 | Mamajek et al. | 128/223 |
| 4,207,893 | 6/1980 | Michaels | 128/260 |
| 4,265,874 | 5/1981 | Bonsen et al. | 424/15 |
| 4,285,987 | 8/1981 | Ayer et al. | 427/3 |
| 4,320,759 | 3/1982 | Theeuwes | 128/260 |
| 4,327,725 | 5/1982 | Cortese et al. | 128/260 |
| 4,449,983 | 5/1984 | Cortese et al. | 604/892 |
| 4,595,583 | 6/1986 | Eckenhoff et al. | 424/15 |
| 4,612,008 | 9/1986 | Wong et al. | 604/892 |
| 4,716,031 | 12/1987 | Eckenhoff | 424/453 |
| 4,814,179 | 3/1989 | Bolton | 424/484 |
| 4,844,905 | 7/1989 | Ichikawa | 424/494 |
| 4,874,388 | 10/1989 | Wong et al. | 604/891.1 |
| 4,925,446 | 5/1990 | Garay et al. | 604/96 |

FOREIGN PATENT DOCUMENTS

202159  11/1986  European Pat. Off. .
265061  4/1988  European Pat. Off. .

OTHER PUBLICATIONS

Tossounian et al. in Drug Dev. Indus. Pharm. (1985) 11:1019–1050.
New Eng. J. Med. (1981) 304:1365–1366.

Primary Examiner—Thurman K. Page
Assistant Examiner—D. Gabrielle Phelau
Attorney, Agent, or Firm—Jacqueline S. Larson; Edward L. Mandell; Steven F. Stone

[57] ABSTRACT

The present invention is directed to a fluid-imbibing drug delivery device having a first, low density such that it floats in the stomach contents for a predetermined prolonged period of time, during which prolonged period of time it dispenses a drug or other active agent to the stomach, and having a second, higher density such that the device exits the stomach at the end of the predetermined prolonged period of time.

6 Claims, 2 Drawing Sheets

SELF-RETAINING GASTROINTESTINAL DELIVERY DEVICE

RELATED APPLICATION

This invention is related to the invention disclosed in copending, commonly-assigned patent application Ser. No. 07/648,270, filed Jan. 30, 1991, abandoned of Wong et al. for Osmotic Device for Delayed Delivery of Agent.

FIELD OF THE INVENTION

The present invention is directed to the field of drug delivery. More particularly, it is related to osmotically-activated devices for administering active agents within the gastrointestinal tract over an extended period of time.

BACKGROUND OF THE INVENTION

The prolonged delivery of active agents orally has been a long-desired objective in drug therapy. It is often desirable to administer a single dose of medication which releases the active ingredient over an extended period of time rather than to administer a number of single doses at regular intervals.

Osmotic dispensing devices for delivery of therapeutically active agents are well known in the art and have been used for the oral administration of drugs. Such devices use an expansion means to deliver an agent to an environment of use over a period of hours, days or months. The expansion means absorbs liquid, expands, and acts to drive out beneficial agent formulation from the interior of the device in a controlled, usually constant manner. The osmotic expansion means is used to controllably, usually relatively slowly, and over a period of time, deliver the agent.

However, long-term oral delivery has been difficult to achieve due to the 8-16 hour gastrointestinal transit time of an ingested substance. In order to achieve uninterrupted action for longer than 24 hours by a therapeutic substance, its passage needs to be slowed in the gastrointestinal tract or the delivery device supplying the drug has to be fixed or immobilized within the tract.

Additionally, certain classes of drugs or active agents are not adequately absorbed during their relatively brief passage through the gastrointestinal tract. This can be due to either their physicochemical properties or their requirement of a particular site of absorption, as is discussed by Tossounian et al. in Drug Dev. Indus. Pharm. (1985) 11:1019-1050. For example, certain drugs are better solubilized in the acidic medium of the stomach rather than in the neutral or alkaline environment of the intestine. Also, many active agents and vitamins are principally absorbed from the upper portion of the small intestine. Other compounds are intended to act in the stomach contents and will lose their beneficial effects if they pass into the intestine.

One method widely used to obtain a necessary or beneficial drug level in the upper gastrointestinal tract over a number of hours comprises administering a number of pills or tablets at regular time intervals to achieve a dose frequency response relationship. However, this method has certain inherent limitations that tend to defeat its purpose. For example, the pills often are rapidly cleared from the gastrointestinal tract before they are fully utilized. Also, the administration of a number of pills at set times over a prolonged period requires attention by the user and frequently a particular administration is inadvertently overlooked, which diminishes the results of this method. Thus, a graphic illustration of the drug's concentration in the blood during a dosage schedule for this method has the appearance of a series of peaks and valleys, rather than a fairly continuous level concentration; and often these valleys may fall below the drug concentration needed to achieve the desired beneficial effects or the peaks rise dangerously above the concentration that is necessary.

Another approach is to provide a sustained release of the agent. Previous sustained release preparations have included active agents that are either coated with varying thicknesses of a relatively insoluble polymer or are embedded into the matrix of water-insoluble ingredients to provide a continuous amount of agent for absorption. However, the dosage forms pass through the gastrointestinal tract without being slowed or immobilized. They are not retained in the stomach for any longer time than a conventional capsule, tablet or pill and hence do not provide administration of drug to the stomach or upper portion of the small intestine for any prolonged period.

Attempts have been made either to incorporate drugs into floating devices which would empty less readily from the stomach (New Eng. J Med. (1981) 304:1365-1366; Tossounian, supra) or to introduce balloon-based devices which could be inflated by propellants or be fluid-expanded in the stomach after the whole device has been swallowed (U.S. Pat. Nos. 3,786,813; 3,788,322; 3,797,429; 3,901,232; 4,207,890; and 4,925,446). One problem with such devices is that often they cannot exit the stomach or exit only with difficulty. This can cause discomfort to the user, and the accumulation of many devices in the stomach can pose serious health problems. Additionally, the rate and/or duration of release of drug from the devices or the duration of the devices within the stomach often cannot be controlled with accuracy. Also, several of these devices are of rather elaborate design, making them difficult to manufacture and expensive.

There remains a continuing need for a practical gastrointestinal drug delivery device that is relatively simple, safe to use, and able to release significant quantities of active agent in a controlled manner over a prolonged period of time into the stomach environment.

SUMMARY OF THE INVENTION

Accordingly, it is an object of the present invention to provide a drug delivery device for the administration of active drugs or agents to the upper gastrointestinal tract, which device essentially overcomes the aforesaid disadvantages associated with the prior art modes of administration.

It is a further object of the invention to provide a drug delivery device for releasing drug or agent to the upper gastrointestinal tract at a controlled rate for a prolonged period of time.

Still another object of the invention is to provide a drug delivery device suitable for continuously administering drug or agent to the stomach and remaining therein until the desired dosage regimen is essentially complete before the device is eliminated from the stomach.

Yet another object of the invention is to provide a drug delivery device that is self-contained and self-powered and will remain in the stomach for an extended time while administering drug or agent from the device.

These and other objects are obtained by the present invention, which is directed to a fluid-imbibing drug delivery device having a first, low density such that it floats in the stomach contents for a predetermined prolonged period of time, during which prolonged period of time it dispenses a drug or other active agent to the stomach, and having a second, higher density such that the device exits the stomach at the end of the predetermined prolonged period of time.

More particularly, the delivery device of the invention comprises a housing formed of at least a first wall section with an open end and a second wall section with an open end, the wall sections being in slidably telescoping arrangement with each other, which housing maintains its integrity in the stomach; an active agent delivery chamber within a portion of the housing, the delivery chamber including at least one active agent formulation, which formulation includes at least one active agent, an exit means for providing communication between the active agent formulation and the stomach environment, and a first expansion means for dispensing the active agent formulation through the exit means to the stomach environment; a bouyancy chamber within a portion of the housing adjacent the open end of the first wall section; and an expansion chamber within a portion of the housing for separating apart the first and second wall sections of the housing after exposure to the stomach environment, the expansion chamber including a second expansion means and a push plate.

The invention also is directed to a method for the controlled administration of a drug or agent to the stomach for a predetermined prolonged period of time, the method comprising placing the delivery device of the invention into the stomach environment, where it floats in the stomach fluids as a result of a first, low density; allowing fluid to be imbibed through at least a portion of the housing of the delivery device for causing the first expansion means to expand to deliver agent formulation into the stomach environment for the predetermined prolonged period of time and for causing the second expansion means to expand to exert pressure on the slidably connected first and second wall sections to push apart and separate the two wall sections after the predetermined prolonged period of time, whereby the density of the device rises, causing the device to lose bouyancy and exit the stomach.

DESCRIPTION OF THE DRAWINGS

The drawings are not drawn to scale, but are set forth to illustrate various embodiments of the invention. Like numbers refer to like structures.

DETAILED DESCRIPTION OF THE INVENTION

The present invention provides a device which is useful for the delivery of an active agent to the upper gastrointestinal tract, the device being maintained in the stomach by means of having a first, low density for a predetermined, prolonged period of time ($t_a$), which low density allows the device to float in the stomach contents, and then exiting the stomach at a later time ($t_b$) by means of converting to a second, higher density.

By "prolonged period of time", as used herein, is meant an extended time period such as for several hours, days, weeks or months.

Figure 1:
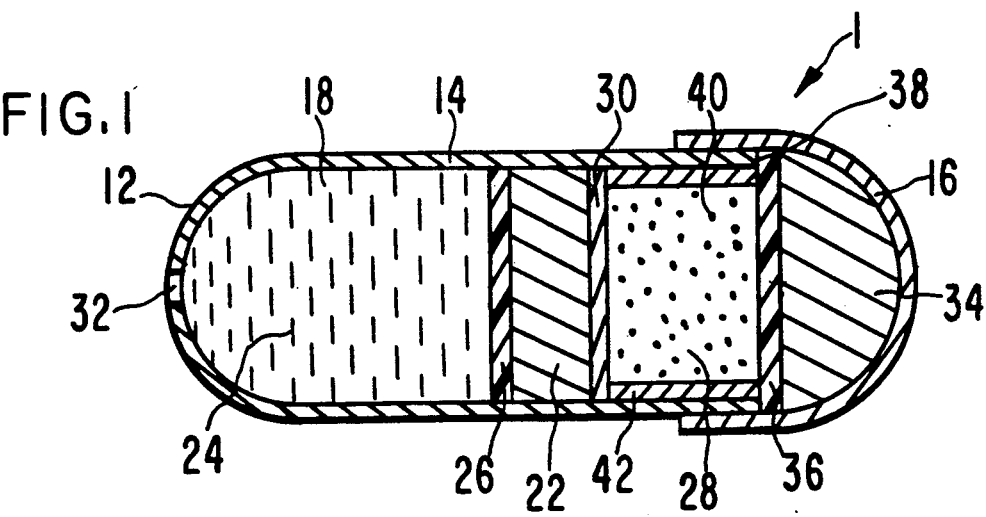
FIG. 1 is a cross-sectional view of one embodiment of the present invention, the device being in closed or prepared form prior to placement in the stomach.

FIG. 1 depicts in cross-sectional view a presently preferred embodiment of the delivery device according to the present invention. The device is shown in closed or prepared form prior to placement in the stomach. Dispensing device 1 comprises a housing 12 formed of a first wall section 14 and a second wall section 16. First wall section 14 and second wall section 16 are in slidably telescoping arrangement with each other. Housing 12 surrounds and defines an internal compartment 18. First wall section 14 surrounds that portion of internal compartment 18 that encompasses the active agent delivery chamber and contains a first expansion means 22 and an active agent formulation 24, which in a preferred embodiment are separated by a movable impermeable partition layer 26 to maintain the separate identities of the agent formulation 24 and the first expansion means 22. That portion of internal compartment 18 surrounded by first wall section 14 also contains a bouyancy chamber 28 adjacent the open end of first wall section 14. Bouyancy chamber 28 contains air, gas or other material 40 for providing a low density (relative to the contents of the stomach) to dispensing device 1 when the device is in its closed or partially opened position, thus allowing the device to float in the contents of the stomach. Because it is necessary that bouyancy chamber 28 be impermeable to fluid from the stomach environment, there is present an impermeable wall 42 in those cases where first wall section 14 as it surrounds the bouyancy chamber is of semipermeable material. Impermeable wall 42 may comprise a ridge or other means for securing and maintaining wall 42 within first wall section 14. Internal compartment 18 further contains impermeable barrier layer 30 which separates first expansion means 22 and the active agent delivery chamber from bouyancy chamber 28. Barrier layer 30 is preferably non-moveable in the device and is of a material which is impermeable to the air, gas or other material in the bouyancy chamber and to fluid or material from the expansion means. First wall section 14 also comprises an exit means or passageway 32 which provides communication between the environment of use and that part of internal compartment 18 containing active agent formulation 24.

That portion of compartment 18 enclosed by second wall section 16 encompasses the expansion chamber and contains a second expansion means 34 and a movable impermeable push layer or push plate 36, push plate 36 being between second expansion means 34 and bouyancy chamber 28.

First wall section 14 and second wall section 16 at their open ends are close in size and they form a friction fit therebetween. The friction generated is sufficient to maintain the two wall sections together prior to activation of the second expansion means 34 but not so great as to keep the two wall sections from sliding apart once an expanding driving force is exerted. First wall section 14 and second wall section 16 can be telescoped completely into a closed and continuous external walled position. The open end of first wall section 14 is adapted to fit within second wall section 16. The bottom edge of the open end of first wall section 14 provides a platform or ridge 38 protruding into compartment 18. Ridge 38 is adapted to receive the driving force of second expansion means 34, via push plate 36, to effect the separation of the two wall sections.

In operation, dispensing device 1 is placed in the stomach environment and first expansion means 22 begins to imbibe and absorb fluid through first wall section 14 from the stomach environment. As means 22 imbibes fluid, it expands and pushes against partition layer 26, and the expanding driving force of means 22 is conveyed via partition layer 26 against active agent formulation 24. Agent formulation 24 is then immediately begun to be expelled in a controlled and continuous manner from internal compartment 18 through exit port 32 into the stomach. The expansion means 22 continues to expand and deliver active agent for a prolonged period of time, $t_a$. At the same time, when device 1 is placed in the stomach, second expansion means 34 also begins to imbibe fluid, through second wall section 16, and expands, exerting a driving force via push plate 36 against end or ridge 38 of first wall section 14 to begin to slidably separate first wall section 14 from second wall section 16. At a point in time $t_b$, which is preferably after the time $t_a$ when substantially all of the active agent formulation 24 has been delivered to the stomach environment, first wall section 14 and second wall section 16 are separated apart from each other by the action of the expansion means 34 on first wall section ridge 38. In such manner, bouyancy chamber 28 is exposed to the stomach environment and the air, gas or other material 40 in the bouyancy chamber is released to the environment.

Figure 2:
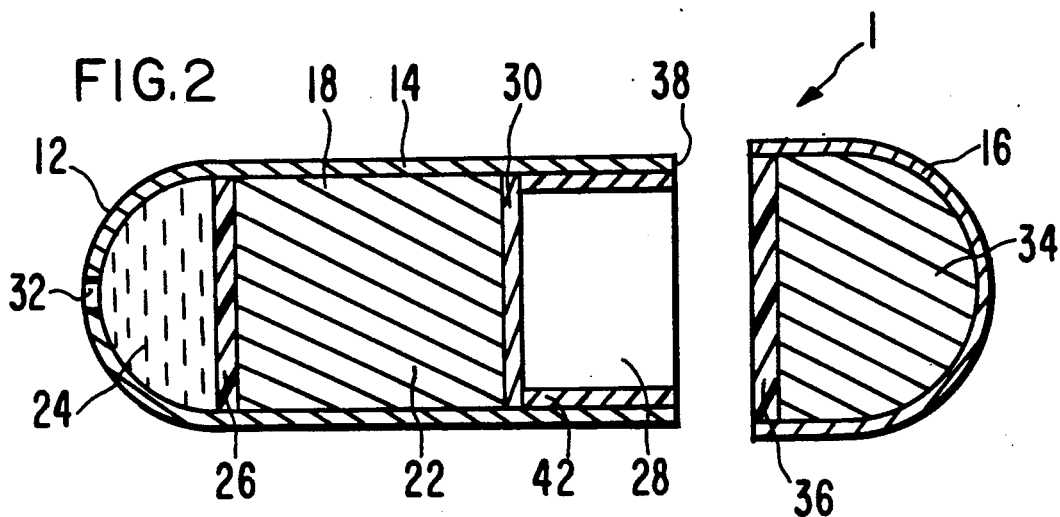
FIG. 2 is the device of FIG. 1 in operation after activation by placement in the stomach, showing the expansion means expanded, the active agent released and the first and second wall sections of the device separated to allow the device to exit the stomach.

This is illustrated in FIG. 2, which shows the dispensing device 1 of FIG. 1 in operation at time $t_a$ after activation of the device by placement in the stomach environment. The release of air or other bouyant material 40 causes the density of the dispensing device 1 to increase relative to the stomach environment to such an extent that the device loses its bouyancy and sinks. Because the dispensing device 1 is now in two smaller portions at a higher density, the portions of the device will easily pass through the pylorus and out of the stomach and be expelled from the body by natural processes.

Figure 3:
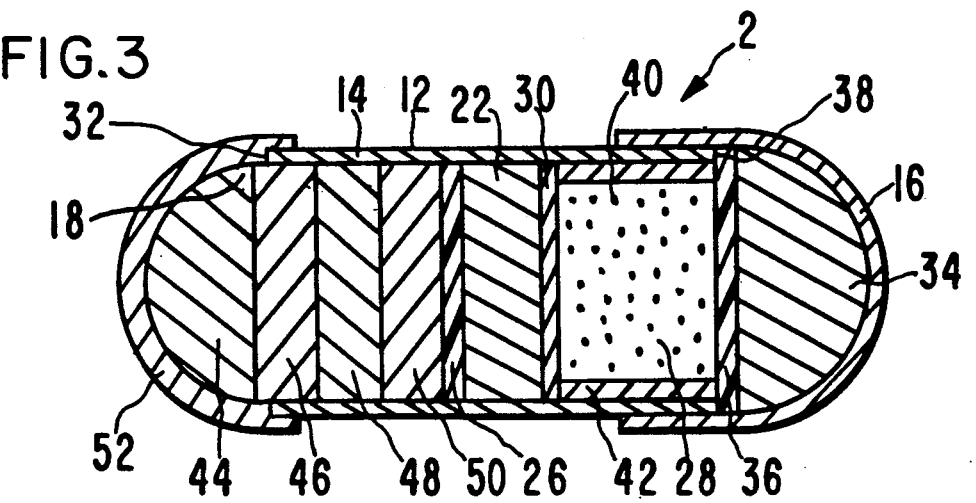
FIG. 3 is a cross-sectional view of another embodiment of the present invention, the device being in closed or prepared form.

FIG. 3 illustrates another embodiment of the device of the invention. As illustrated in this figure, dispensing device 2 is similar to dispensing device 1 of FIGS. 1 and 2, having a housing 12, a first wall section 14 with a ridge 38, a second wall section 16, an internal compartment 18 surrounded and defined by housing 12, first expansion means 22, second expansion means 34, partition layer 26, push plate 36, bouyancy chamber 28 with air, gas or other bouyant material 40 and impermeable wall 42, barrier layer 30, and exit means 32. In dispensing device 2, the active agent formulation is present as a plurality of active agent dosage forms 44, 46, 48 and 50. Although four dosage forms are illustrated, the number is not critical and any number of dosage forms are included under the invention. Optionally, layers of a barrier material (not shown) may be placed between the agent dosage forms in alternating arrangement to provided a pulsed delivery. The exit means or passageway 32 may optionally be closed by an erodible material 52 such as, for example, microscrystalline wax or gelatin, for protecting the active agent formulation prior to placing in the stomach environment, or there may optionally be present a retaining structure such as a screen or mesh for retaining the dosage forms within the device until they are dispensed into the environment.

Figure 4:
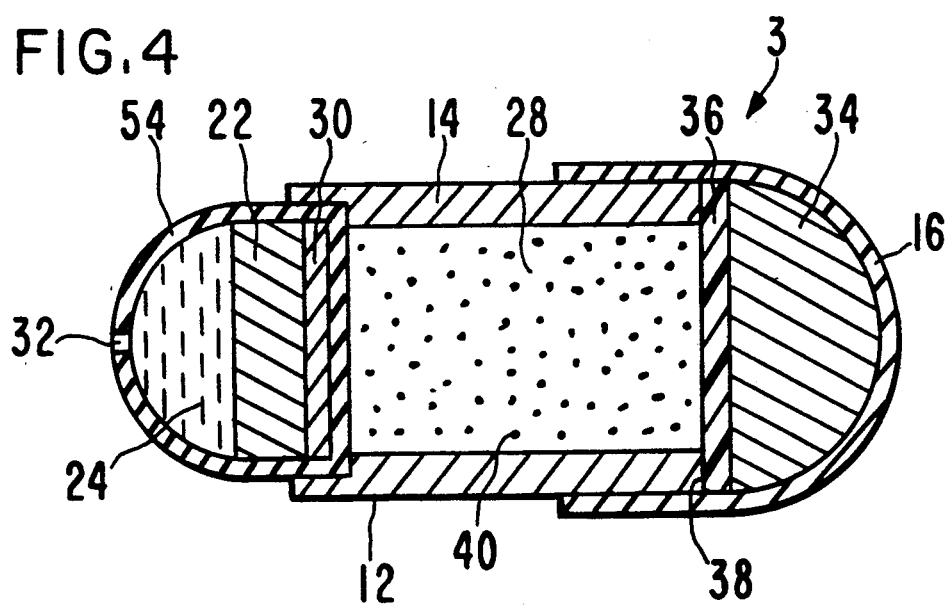
FIG. 4 is a cross-sectional view of a further embodiment of the present invention, the device being in closed or prepared form.

FIG. 4 illustrates another embodiment of the invention. In dispensing device 3, housing 12 is formed not only of first wall section 14 and second wall section 16, but also of a third wall section 54. Third wall section 54 comprises the active agent delivery chamber and contains first expansion means 22 and active agent formulation 24 and includes exit means 32. First wall section 14 encloses bouyancy chamber 28, with air, gas or other bouyant material 40, and therefore is preferably composed of an impermeable material in dispensing device 3. An impermeable barrier layer 30 is positioned between first expansion means 22 and bouyancy chamber 28. Second wall section 16 comprises the expansion chamber and contains second expansion means 34 and push plate 36, which is positioned against ridge 38 of the first wall section 14. The embodiment of dispensing device 3 is desirable when an agent dispensing unit or third wall section 54 is assembled as a separate unit from the remainder of the device and is then attached to first wall section 14 by, for example, solvent bonding, adhesive bonding or heat bonding.

Because first expansion means 22 operates by the imbibition of external fluid, first wall section 14 in at least a portion adjacent first expansion means 22 must comprise a composition that is semipermeable; that is, it is permeable to fluid but impermeable to active agent and other ingredients contained in the dispensing device. When an active agent or an active agent dosage form is sensitive to fluid from an exterior fluid present in the environment of use, it is preferred that first wall section 14 be substantially impermeable to the ingress of the external fluid in a portion adjacent the active agent formulation to serve as a means for substantially protecting the agent or dosage form. When first wall section 14 encompasses only bouyancy chamber 28 (as illustrated in FIG. 4), all of first wall section 14 is comprised of an impermeable composition.

Because second expansion means 34 also operates by the imbibition of external fluid, second wall section 16 in at least a portion that is adjacent to second expansion means 34 must be semipermeable; that is, it is permeable to the passage of fluid while being substantially impermeable to the passage of other ingredients contained in dispensing device.

Third wall section 54, when present, is comprised of a semipermeable composition.

Wall sections 14, 16 and 54 optionally comprise additional ingredients such as, for example, a plasticizer. Impermeable and semipermeable compositions suitable for use in wall sections 14, 16, or 54, as well as suitable additives, are known in the art, examples of which are disclosed in U.S. Pat. No. 4,874,388, the entire disclosure of which is incorporated herein by reference.

Housing 12 is nontoxic, biologically inert, nonallergenic and nonirritating to body tissue, and it maintains its physical and chemical integrity; that is, housing 12 does not erode or degrade in the environment of use during the dispensing period. It is within the scope of the invention that the housing be insoluble only during the period of intended use and can thereafter dissolve away in the environment of the device. Thus, a dispenser is here contemplated which is unaffected by its environment, solubility-wise, at the situs of use or which, alternatively, is only slightly soluble during the period of intended use, such that once its active agent content has been removed it will then dissolve or erode away.

The first and second expansion means or expandable driving means 22 and 34 are nontoxic, nonallergenic and biologically inert. Expansion means 22 and 34 may be the same or they may be different. In one presently preferred embodiment, means 22 and/or 34 comprises an osmopolymer. The osmopolymers interact with water and aqueous biological fluids and swell or expand to an equilibrium state. The osmopolymers exhibit the ability to swell in fluid and to retain a significant portion of the imbibed and absorbed fluid within the polymer structure. The expansion means 22 and/or 34 in another preferred embodiment comprises an osmagent. The osmagents are known also as osmotically effective solutes and they are also known as osmotically effective compounds. The osmagents that can be used for the purpose of this invention include inorganic and organic compounds that exhibit an osmotic pressure gradient across a semipermeable, i.e. a fluid-permeable, wall. The expansion means 22 and/or 34 in yet another preferred embodiment comprises an osmagent dispersed within an osmopolymer. The expansion means can comprise a tablet or a layer, or a plurality of tablets or layers, and be placed into position in the device or it can be pressed into the appropriate wall section. The osmagent or osmopolymer can be in any suitable form such as particles, crystals, pellets, granules, and the like, when pressed into a tablet layer and into the wall section. Osmagents and osmopolymers are known to the art and are described in, for example, U.S. Pat. Nos. 3,865,108, 4,002,173, 4,207,893, 4,327,725 and 4,612,008.

Partition layer 26 and push plate 36, in a presently preferred embodiment, each comprises a composition that is substantially impermeable to the passage of fluid, and they serve to restrict the passage of fluid present in the expansion means into other areas of compartment 18. They operate to essentially maintain the integrity of the active agent formulation 24 or the bouyancy chamber 28 and the expansion means layers. Additionally, and importantly, push plate 36 acts to insure that the expanding driving force generated by the second expansion means 34 is applied directly against the first wall section 14 to effect the separation of the two wall sections. Thus, push plate 36 must be of sufficient strength, thickness and rigidity to transfer the driving force against first wall section 14.

Representative impermeable materials useful as a partition layer 26, a barrier layer 30 or push plate 36 are known to the art in, for example, U.S. Pat. No. 4,874,388.

The term "active agent formulation", as used herein, comprises the active agent to be delivered, as a liquid, solid, semisolid or thermosensitive composition, generally in a carrier substance and with or without additional inert ingredients. The term may additionally include dosage forms comprising the active agent which are capable of maintaining their physical configuration and chemical integrity while housed within the dispenser. These include, without limitation, tablets with or without a density element; matrix tablets; spheres; pellets and elongated tablets; capsules; elementary osmotic pumps, such as those described in U.S. Pat. No. 3,845,770; mini-osmotic pumps, such as those described in U.S. Pat. Nos. 3,995,631, 4,034,756 and 4,111,202; and multichamber osmotic systems referred to as push-pull and push-melt osmotic pumps, such as those described in U.S. Pat. Nos. 4,320,759 and 4,449,983; all the above patents of which are incorporated herein by reference.

The pharmaceutically acceptable carrier useful herein may comprise more than one ingredient, such as, for example, a buffer, a viscosity regulating vehicle, a surfactant, dyes, a permeation enhancer, proteinase inhibitors, or other formulation ingredients and additives, as are known in the art. The carrier may contain more than one active agent. The active agent formulation can erode or disintegrate and can be in the form of a wax formulation, solid core or tablet, for example. The formulation can immediately dissolve upon exposure to fluid or it may erode slowly with or without the presence of excipients for controlling erosion.

The active agent formulation can be designed in a multitude of ways to provide a specific drug delivery profile. One embodiment may comprise a formulation that contains a biologically acceptable solid surfactant which is capable of slow dispersion in the environmental fluid. In another embodiment, the formulation may contain a fluid-insoluble wax and a surfactant so that the formulation is susceptible to erosion in the environment. In still another embodiment, the formulation may be effervescent and provide drug delivery in a finely dispersed form. This is accomplished by the addition of a solid basic compound capable of evolving carbon dioxide in the presence of an acid in the environment of use. Suitable basic compounds are disclosed in U.S. Pat. No. 4,265,874. In a further embodiment, the formulation may include an osmotic agent or solute, such as those described above with reference to the expansion means 22, so that when the formulation comes into contact with the environmental fluid, it immediately dissolves. In yet another embodiment, the agent formulation can be comprised of an agent and a thermoresponsive composition. In this manner, the formulation would exhibit solid-like properties at room temperature of 21° C. and within a few degrees Celsius thereof, and would have a melting point that approximates mammalian body temperatures of 37° C. and within a few degrees Celsius thereof. The term "thermoresponsive" as used herein in a preferred embodiment denotes the physical-chemical property of an agent carrier composition to exhibit solid, or solid-like properties at temperatures up to 31° C. and become fluid, semi-solid or viscous when disturbed by heat at temperatures from 31° C., usually in the range of 31° C. to 45° C. Suitable materials useful as active agent carriers and excipients are known in the art and are disclosed in U.S. Pat. Nos. 4,595,583 and 4,874,388, for example.

The terms "active agent" and "drug" are used interchangeably herein and refer to an agent, drug, compound, composition of matter or mixture thereof which provides some therapeutic, often beneficial, effect. This includes pesticides, herbicides, germicides, biocides, algicides, rodenticides, fungicides, insecticides, antioxidants, plant growth promoters, plant growth inhibitors, preservatives, antipreservatives, disinfectants, sterilization agents, catalysts, chemical reactants, fermentation agents, foods, food supplements, nutrients, cosmetics, drugs, vitamins, sex sterilants, fertility inhibitors, fertility promoters, microorganism attenuators and other agents that benefit the environment of use. As used herein, the terms further include any physiologically or pharmacologically active substance that produces a localized or systemic effect or effects in animals, including warm blooded mammals, humans and primates; avians; domestic household or farm animals such as cats, dogs, sheep, goats, cattle, horses and pigs; laboratory animals such as mice, rats and guinea pigs; fish; reptiles; zoo and wild animals; and the like. The active drug that can be delivered includes inorganic and organic compounds, including, without limitation, those materials that act upon the central nervous system such as hypnotics and sedatives, psychic energizers, tranquilizers, anticonvulsants, muscle relaxants, antiparkinson agents, analgesics, anti-inflammatories, local anesthetics, muscle contractants, antispasmotics, anti-ulcer agents, antimicrobials, antimalarials, hormonal agents including contraceptives, antihistamines, sympathomimetrics, polypeptides and proteins capable of eliciting physiological effects, diuretics, lipid regulating agents, steroids, cardiovascular drugs, antiandrogenic agents, antiparasitics, neoplastics, antineoplastics, hypoglycemics, nutritional agents and supplements, vitamins, growth supplements, fats, ophthalmics, antienteritis agents, electrolytes and diagnostic agents.

It is to be understood that more than one active agent may be incorporated into the active agent formulation in a device of this invention, and that the use of the term "agent" or "drug" in no way excludes the use of two or more such agents or drugs.

The agents can be in various forms, such as uncharged molecules, components of molecular complexes or nonirritating, pharmacologically acceptable salts. Also, simple derivatives of the agents (such as ethers, esters, amides, etc.) which are easily hydrolyzed by body pH, enzymes, etc., can be employed.

The amount of active agent employed in the delivery device will be that amount necessary to deliver a therapeutically effective amount of the agent to achieve the desired result at the site of delivery. In practice, this will vary widely depending upon the particular agent, the site of delivery, the severity of the condition, and the desired therapeutic effect. Thus, it is not practical to define a particular range for the therapeutically effective amount of active agent incorporated into the device.

As used herein, the terms "therapeutically effective" amount or rate refer to the amount or rate of the active agent needed to effect the desired therapeutic, often beneficial, result.

The terms "exit means" and "exit passageway", as used herein, comprise means and methods suitable for the metered release of the active agent formulation from compartment 18 of the delivery device of the present invention. The exit means 32 includes at least one passageway, orifice, or the like, through first wall section 14 for communicating with compartment 18. The expression "at least one passageway" includes aperture, orifice, bore, pore, porous element through which the agent can migrate, hollow fiber, capillary tube, porous overlay, porous insert, and the like. The expression also includes material that is discharged, erodes or is leached from the wall in the fluid environment of use to produce at least one passageway in the delivery device. Representative materials suitable for forming at least one passageway, or a multiplicity of passageways, include an erodible poly(glycolic) acid or poly(lactic) acid member in the wall; a gelatinous filament; poly(vinyl alcohol); leachable materials such as fluid-removable pore-forming polysaccharides, salts, or oxides; erodable or dischargable materials such as natural and synthetic waxes; and the like. The expression includes structural characteristics that concentrate stress at a precise point in the wall so that only a small amount of force will induce breakage in the wall, yielding a passageway through the wall from compartment 18 to the outside of the device. A passageway or a plurality of passageways can be formed by leaching a material such as sorbitol, lactose and like water-soluble solids from the wall. A passageway or passageways can be formed by the discharge, as a result of the pressure created by the expandable driving means for example, of a material such as a wax. The exit means or passageway can have any shape such as round, triangular, square, elliptical, and the like, for assisting in the metered release of active agent from the delivery device. The delivery device can be constructed with one or more passageways in spaced-apart relations or more than a single surface of a dosage form. Passageways and equipment for forming passageways are disclosed in U.S. Pat. Nos. 3,845,770; 3,916,899; 4,063,064; and 4,088,864. Passageways formed by leaching are disclosed in U.S. Pat. Nos. 4,200,098 and 4,285,987.

The initial low density, relative to the stomach environment, of the dispensing device according to the present invention is provided by the presence of a material such as air or a gas in the bouyancy chamber 28 when the device is in its closed configuration. This low density allows the device to float within or on the surface of the stomach contents so that the device will remain in the stomach for a prolonged period while it dispenses its active agent into the stomach environment. The low density generally is in the range of from about 0.5 to about 0.7. The particular low density of the device is determined by the size of bouyancy chamber 28 relative to the overall size of the device. A larger bouyancy chamber results in a larger amount of air, gas or other bouyant material present in the device, which in turn results in a more bouyant device. A larger bouyancy chamber relative to the overall device will have a corresponding lower drug or active agent loading.

At a point in time after delivery of the active agent has substantially concluded, the two wall sections of the device are separated apart by the expansion of expansion means 34 to open the bouyancy chamber to the stomach environment, allowing the air, gas or other bouyant material to escape into the environment. This functions to increase the density of the device so that the device sinks and exits the stomach. Such a higher density is generally in the range of from about 1.2 to about 1.4. Separation of the two wall sections according to this invention also functions to provide two smaller units which may even more easily pass out of the stomach.

The total delivery time of the active agent formulation and the total delay time prior to separation of the dispensing device can be controlled by a number of means. For example, the rate of fluid imbibition into the expansion means can be controlled by the particular choice of semipermeable membrane. The rate of expansion of the expansion means can be controlled by the choice of composition of the expansion means. The distance of overlap between the open end portions of the first and second wall sections can determine the period of time required for the two sections to separate. Combinations of such means may be used. Such control means are known in the art and can be determined without undue experimentation.

The delivery device of the present invention can be manufactured by standard manufacturing techniques. For example, in the preparation of devices of the present invention, first wall section 14 (the vessel) and second wall section 16 (the cap) may be separately molded or extruded to the desired shape. Possible semipermeable materials from which the wall sections may be prepared include, for example, Hytrel polyester elastomer (Du Pont), cellulose esters, ethylene-vinyl acetate copolymer and other semipermeable materials known to the art. Alternatively, the two portions of a hard gelatin capsule may be coated with a semipermeable material such as cellulose ester-based polymer mixtures. In a presently preferred embodiment, the assembled device in closed configuration is about the size and dimensions of a size "0" to size "00" hard gelatin capsule. The exit means 32 may be formed during the molding process or may be drilled after the vessel portion has been made.

Impermeable wall 42 may be prepared as an extruded tube cut to the correct length or as a tube molded to shape with an outer diameter that is approximately the same as the inside diameter of first wall section or vessel 14. Impermeable materials from which the wall 42 may be prepared include, for example, polyethylene, polystyrene, cellulose triacetate, Hytrel polyester elastomer (Du Pont) and other impermeable materials known to the art. The length of the tube will determine the length of the air pocket or chamber within the closed device.

A "bilayer osmotic plug" composed of second osmotic layer or expansion means 34 and impermeable push plate 36 is prepared in a shape that will fit within cap 16. The osmotic plug is compressed on a bilayer rotary tablet press.

A "trilayer osmotic plug" composed of impermeable partition layer 26, first osmotic layer or expansion means 22 and impermeable barrier layer 30 is prepared in a shape that will fit within vessel 14. The three layers are compressed into a tablet on a rotary trilayer tablet press.

The device is assembled by first placing a soluble seal or a hard gelatin cap over exit means 32 in vessel 14. Active agent formulation 24 is then placed in the vessel at its open end; the formulation may be in the form of a liquid, semi-solid, powder or shaped tablet or tablets. The trilayer osmotic plug is then inserted on top of the agent formulation, taking care that the least possible air gap exists between the agent fill and the trilayer osmotic plug. Impermeable tube 42 is then placed in vessel 14 in such manner that the tube's final position has its external end flush with the end of the vessel and its internal end flush with the barrier layer portion of the trilayer osmotic plug. The spacer tube may be locked into place by adhesive bonding or by molded ribs. The bilayer osmotic plug is placed within the cap 16 and the cap assembly is placed over the open end of the filled vessel 14, to give a device as illustrated in FIG. 1. In an alternative assembly method, the device may be assembled as described above, but without addition of the active agent formulation. After assembly is completed, the device is oriented with the cap portion downwards and liquid or molten agent formulation is placed in the vessel portion through orifice 32. After filling, the open orifice may be sealed, if desired.

When the device of the invention has the configuration of FIG. 3, it may be prepared by molding or extruding a semipermeable first wall section or vessel 14 with two open ends. The impermeable tube 42 is fitted flush to one end of the vessel cylinder and fixed within the cylinder (by adhesive bonding, for example). The semipermeable second wall section or cap 16 containing the bilayer osmotic tablet (prepared as described above) is then placed over the tube-containing end of the vessel. The trilayer osmotic plug (as above) is inserted through the other or drug delivery end of the vessel and is placed flush with the tube 42. The remainder of the vessel portion is then filled with active agent, typically in the form of one or more active agent tablets. The active agent tablets may optionally be separated by non-active agent-containing layers or tablets to provide a pulsed delivery of agent to the stomach environment. After all agent formulation has been placed in the vessel, a cap, screen or other covering may be placed over the open end, if desired.

The following example is illustrative of the present invention. It is not to be construed as a limitation of the scope of the invention. Variations and equivalents of this example will be apparent to one skilled in the art in light of the present disclosure, the drawings and the claims herein.

EXAMPLE 1

A delivery device according to the present invention is prepared as follows.

The first osmotic engine portion of the device is a compressed trilayer tablet composed of a 50 mg wax-based barrier layer, 200 mg of a polymeric osmotic formulation (first expansion means) and a 50 mg wax-based partition layer.

The polymeric osmotic formulation has a composition of 59.5 wt % polyethylene oxide (Polyox ® 303, Union Carbine), 29 wt % sodium chloride, 5 wt % polyacrylic acid (Carbomer ® 934P, B. F. Goodrich), 5 wt % hydroxypropylmethylcellulose E-5 (Aqualon) and 1 wt % ferric oxide. During preparation, each of the above components is screened through a 40 mesh screen, and the sized components are added to a mixing vessel in the appropriate proportions. The dry components are mixed thoroughly for 10 minutes; then, ethanol is slowly added while mixing until a wet mass has formed. The wet mass is then screened through a 20 mesh screen, and the wet granules are allowed to air dry for 18 hours. After drying, the granules are passed once more through a 20 mesh screen. Magnesium stearate (0.5 wt %) is then added to the granulation and the granulation is mixed thoroughly for 5 min.

The barrier layer and the partition layer each has a composition of 95 wt % microcrystalline wax (MF-2JH Durawax ®, Astor Wax Corp.) and 5 wt % gelatin (Type A, 250–300 bloom, Knox Gelatin). During preparation, each component is screened through a 40 mesh screen before being added in the correct weight ratio to a mixing vessel. The dry materials are then mixed thoroughly for 10 minutes, after which purified water is slowly added to the mixture while stirring is continued. After a wet mass has formed, the mixture is passed through a 20 mesh screen, and the granules are oven-dried at 40° C. for 24 hours. After the granules have dried, they are rescreened through a 20 mesh screen.

The wax formulation (50 mg) for the barrier layer, the osmotic formulation (200 mg) and the wax formulation (50 mg) for the partition layer are compressed together in a rotary press into a cylindrical trilayer tablet with both the barrier face and the partition face of the tablet being flat. Tabletting is conducted to produce a clean, distinct interface between the three layers.

The second osmotic engine portion of the device is a compressed bilayer tablet composed of a 50 mg wax-based push plate and 150 mg of a polymeric osmotic formulation (second expansion means). The composition of the second osmotic formulation is the same as that for the first osmotic formulation above, and the composition of the push plate is the same as that for the barrier and partition layers above. The osmotic formulation (150 mg) and the wax push plate formulation (50 mg) are compressed in a rotary press into a cylindrical bilayer tablet. The osmotic face of the tablet is convex, to conform to the shape of the device, while the push plate face of the tablet is flat. Tabletting was conducted to produce a clean, distinct interface between the two layers.

To prepare the vessel portion (first wall section) of the device, 70 wt % cellulose acetate 320 and 30 wt % polypropylene glycol are thoroughly mixed together and the mixture is added to the hopper of a screw extruder. The polymeric mixture is heated at 127° C. as it is extruded through the heated barrel of the extruder and is extruded into a mold for the vessel. The polymer mixture is allowed to cool after injection into the mold, after which the vessel is removed. An exit orifice is drilled through the closed end of the vessel.

The cap portion (second wall section) of the device is prepared in the same manner as the vessel, and having the same composition as the vessel. The heated polymeric mixture is injected into a mold for the cap and allowed to cool, and the finished cap is then ejected.

The barrier tube for the bouyancy chamber, having a composition of polyethylene, is prepared by placing the polyethylene in an extruder with a barrel temperature of 130° C. and extruding the material in a tube shape. After extrusion, the tube is cut to the desired length for the chamber and is allowed to cool.

To assemble the delivery device, the exit orifice in a completed vessel portion is sealed with microcrystalline wax by dipping the end in the melted wax and allowing it to cool for about 20 seconds, after which the excess wax is wiped off. The desired active agent formulation is placed into the vessel by manual or automated fill mechanisms. An osmotic trilayer tablet is placed into the vessel in contact with the agent formulation. A bouyancy chamber tube is then placed into the vessel, having its internal end flush with the trilayer tablet and its external end flush with the open end of the vessel. A ridge around the circumference of the tube fits into a corresponding locking groove in the internal wall of the vessel, securing the fitted tube in place. Next, an osmotic engine bilayer tablet is placed into a completed cap, with the convex osmotic layer pointed into the closed end of the cap and the push plate exposed toward the cap opening. The open end of the filled vessel is fitted inside the open end of the cap, and the two pieces are compressed together until cap, osmotic bilayer tablet and vessel fit together tightly.

The above description has been given for ease of understanding only. No unnecessary limitations should be understood therefrom, as modifications will be obvious to those skilled in the art.

What is claimed is:

1. A fluid-imbibing delivery device for dispensing an active agent to the stomach environment over a predetermined prolonged period of time of from several hours to months, wherein the device has a first, low density relative to the stomach environment of from about 0.5 to about 0.7 such that it floats in the stomach contents for the predetermined prolonged period of time, during which prolonged period of time it dispenses the active agent to the stomach, and has a second, higher density of from about 1.2 to about 1.4 such that the device sinks in and exits the stomach at the end of the predetermined prolonged period of time, the device comprising:
    (a) a housing comprising at least a first wall section and a second wall section, the first and second wall sections being in reversibly sliding telescoping arrangement with each other, the first wall section having an open end adapted to fit within the second wall section, which housing maintains its integrity in the stomach environment;
    (b) an active agent delivery chamber within the housing comprising
        (i) at least one active agent formulation,
        (ii) a first expansion means comprising an osmopolymer, an osmagent, or a mixture of an osmopolymer and an osmagent, and
        (iii) an exit means;
    (c) a bouyancy chamber within the housing, the bouyancy chamber having an open end defined by the open end of the first wall section; and
    (d) an expansion chamber within the housing for separating apart the first and second wall sections after the predetermined prolonged period of time, the expansion chamber comprising
        (i) a second expansion means comprising an osmopolymer, an osmagent, or a mixture of an osmopolymer and an osmagent, and
        (ii) a push plate adjacent the open end of the first wall section.

2. A delivery device according to claim 1 which further comprises a partition layer between the active agent formulation and the first expansion means.

3. A delivery device according to claim 1 wherein the first wall section and the second wall section is each comprised of a semipermeable composition, and the device further comprises an impermeable wall within the bouyancy chamber and adjacent the walls of the first wall section.

4. A method for delivering an active agent to the stomach environment for a predetermined prolong period of from several hours to months, the method comprising:
    (1) placing a delivery device into the stomach environment, where it floats in the stomach fluids as a result of a first, low density relative to the stomach environment of from about 0.5 to about 0.7, where the delivery device comprises:
        (a) a housing comprising at least a first wall section and a second wall section, the first and second wall sections being in reversibly sliding telescoping arrangement with each other, the first wall section having an open end adapted to fit within the second wall section, which housing maintains its integrity in the stomach environment;
        (b) an active agent delivery chamber within the housing comprising
            (i) at least one active agent formulation,
            (ii) a first expansion means comprising an osmopolymer, an osmagent, or a mixture of an osmopolymer and an osmagent, and
            (iii) an exit means;
        (c) a bouyancy chamber within the housing, the bouyancy chamber having an open end defined by the open end of the first wall section; and (d) an expansion chamber within the housing for separating apart the first and second wall sections after the predetermined prolonged period of time, the expansion chamber comprising
  (i) a second expansion means comprising an osmopolymer, an osmagent, or a mixture of an osmopolymer and an osmagent, and
  (ii) a push plate adjacent the open end of the first wall section;
(2) allowing fluid to be imbibed through at least a portion of the housing of the delivery device for causing the first expansion means to expand to deliver agent formulation into the stomach environment for the predetermined prolonged period of time and for causing the second expansion means to expand to exert pressure on the slidably connected first and second wall sections to push apart and separate the two wall sections after the predetermined prolonged period of time, whereby the density of the device rises to from about 1.2 to about 1.4, causing the device to sink and exit the stomach.

5. A method according to claim 4 wherein the delivery device further comprises a partition layer between the active agent formulation and the first expansion means.

6. A method according to claim 4 wherein the first wall section and the second wall section is each comprised of a semipermeable composition, and the device further comprises an impermeable wall within the bouyancy chamber and adjacent the walls of the first wall section.

* * * * *